US00RE40681E

(19) United States
(12) Reissued Patent
Pitzen et al.

(10) Patent Number: US RE40,681 E
(45) Date of Reissued Patent: Mar. 24, 2009

(54) COMBINATION RECHARGEABLE, DETACHABLE BATTERY SYSTEM AND POWER TOOL

(75) Inventors: James F. Pitzen, Maplewood, MN (US); Jeffrey D. Smith, Marine on Saint Croix, MN (US); Charles E. Alexson, Hayward, WI (US)

(73) Assignee: Linvatec Corporation, Largo, FL (US)

(21) Appl. No.: 11/129,760

(22) Filed: May 16, 2005

(Under 37 CFR 1.47)

Related U.S. Patent Documents

Reissue of:
(64) Patent No.: 5,792,573
Issued: Aug. 11, 1998
Appl. No.: 08/692,886
Filed: Jul. 24, 1996

U.S. Applications:
(60) Continuation of application No. 09/954,526, filed on Mar. 5, 2001, which is a continuation of application No. 09/637,339, filed on Aug. 11, 2000, now abandoned, which is a division of application No. 08/258,338, filed on Jun. 10, 1994, now Pat. No. 5,553,675.

(51) Int. Cl.
*H01M 2/10* (2006.01)

(52) U.S. Cl. ..... 429/97; 429/98; 429/99; 429/100

(58) Field of Classification Search ..... None
See application file for complete search history.

(56) References Cited

U.S. PATENT DOCUMENTS

| | | | | |
|---|---|---|---|---|
| 1,036,063 A | | 8/1912 | Bedell et al. | |
| 1,152,247 A | | 8/1915 | Walker | |
| 2,104,772 A | | 1/1938 | Saunders | |
| 2,261,230 A | * | 11/1941 | Cox et al. | 606/180 |
| 2,460,149 A | * | 1/1949 | Schoensiegel | 74/421 A |
| 3,079,510 A | | 2/1963 | Hartwig | |

(Continued)

FOREIGN PATENT DOCUMENTS

| | | | |
|---|---|---|---|
| DE | 3 317 398 | * | 10/1985 |
| DE | 3317398 | * | 10/1985 |
| DE | 93 19 361 U1 | | 3/1994 |
| DE | 9319361 | * | 3/1994 |
| EP | 0 272 434 | * | 6/1988 |
| EP | 0272434 | * | 6/1988 |

OTHER PUBLICATIONS

Japanese Abstract, 1484694, Portable Drills, Aug. 27, 1974. (1 Page).*

Product brochure entitled "Maxion™ Cordless Powered Instrument System", by 3M HealthCare, (31 pages). (No date).*

Product brochure entitled: "The K–100 Mini–Driver System. Cleaning and Lubrication", by 3M Surgical Products Division (5 pages). (No Date).*

Product brochure entitled: "Cordless 800 Wire Driver", by Dyonics, 1984, (2 pages) (No month).*

Product brochure entitled: "Cordless 200 Reamer" by Dyonics, 1984. (2 pages). (No month).*

Product brochure entitled "Cordless 450 Orthopedic Drill", by Dyonics. 1984. (2 pages) (No month).*

(Continued)

*Primary Examiner*—John S Maples
(74) *Attorney, Agent, or Firm*—Hunton & Williams LLP

(57) ABSTRACT

[A cordless drive assembly for driving various orthopedic surgical instruments is described. The drive assembly is battery powered and includes tracks in the handle portion of its housing for receiving the battery. A latch locks the battery to the housing.]

*A combination of a rechargeable, detachable battery system and a power tool. The battery slides onto the power tool through a complementary groove and flange structure.*

24 Claims, 9 Drawing Sheets

U.S. PATENT DOCUMENTS 3,120,845 A * 2/1964 Horner ..... 606/180
3,186,878 A 6/1965 Filander
3,494,799 A * 2/1970 Pedone, Jr. ..... 307/150
3,734,207 A * 5/1973 Fisbein ..... 173/217
3,757,194 A 9/1973 Weber et al.
3,767,468 A 10/1973 Schusler
3,883,789 A 5/1975 Achenbach et al.
3,943,934 A 3/1976 Bent
3,952,239 A 4/1976 Owings et al.
3,973,179 A 8/1976 Weber et al.
3,999,110 A * 12/1976 Ramstrom et al. ..... 320/112
4,050,528 A * 9/1977 Foltz et al. ..... 173/217
4,091,880 A * 5/1978 Troutner et al. ..... 173/217
4,386,609 A * 6/1983 Mongeon ..... 606/53
4,388,582 A 6/1983 Saar et al.
4,392,101 A 7/1983 Saar et al.
4,441,563 A * 4/1984 Walton, II ..... 173/213
4,447,749 A * 5/1984 Reeb, Jr. et al. ..... 310/71
4,517,263 A 5/1985 Reiss et al.
4,522,898 A 6/1985 Esrom
4,555,849 A 12/1985 Ando et al.
4,563,629 A 1/1986 Keiper
4,576,880 A 3/1986 Verdier et al.
4,616,169 A 10/1986 Proffitt
4,616,171 A 10/1986 Hernandez et al.
4,672,292 A 6/1987 Hernandez
4,716,352 A 12/1987 Hurn et al.
4,728,876 A * 3/1988 Mongeon et al. ..... 320/114
4,736,742 A * 4/1988 Alexson et al. ..... 606/80
4,749,049 A 6/1988 Greppmair
4,751,452 A * 6/1988 Kilmer et al. ..... 320/106
D300,132 S 3/1989 Culbertson et al.
4,834,092 A * 5/1989 Alexson et al. ..... 606/1
4,835,410 A * 5/1989 Bhagwat et al. ..... 307/64
4,847,513 A 7/1989 Katz et al.
4,853,607 A 8/1989 Walter et al.
D304,026 S 10/1989 Goodner et al.
4,871,629 A * 10/1989 Bunyea ..... 429/97
4,873,461 A * 10/1989 Brennan et al. ..... 310/47
4,904,549 A 2/1990 Goodwin et al.
4,930,583 A 6/1990 Fushiya et al.
D310,813 S 9/1990 Culbertson et al.
4,957,831 A 9/1990 Meredith et al.
4,981,108 A 1/1991 Faeroe
5,013,993 A 5/1991 Bhagwat et al.
5,026,384 A * 6/1991 Farr et al. ..... 606/159
5,043,650 A 8/1991 Bhagwat et al.
D320,917 S 10/1991 Fushiya et al.
D320,974 S 10/1991 Culbertson
5,054,563 A 10/1991 Zapf
5,059,885 A 10/1991 Weiss et al.
D323,276 S 1/1992 Fushiya et al.
5,080,983 A 1/1992 Alexon et al.
5,089,738 A * 2/1992 Bergqvist et al. ..... 310/50
5,095,259 A 3/1992 Bailey et al.
5,122,427 A * 6/1992 Flowers et al. ..... 429/97
5,136,469 A * 8/1992 Carusillo et al. ..... 361/720
5,140,249 A 8/1992 Linder et al.
5,144,217 A 9/1992 Gardner et al.
5,148,094 A 9/1992 Parks et al.
5,149,230 A 9/1992 Nett
5,169,225 A 12/1992 Palm
5,200,280 A 4/1993 Karasa
5,207,697 A * 5/1993 Carusillo et al. ..... 606/167
5,208,525 A 5/1993 Lopic et al.
5,213,913 A * 5/1993 Anthon et al. ..... 429/97
5,221,210 A 6/1993 Bormuth et al.
5,229,702 A 7/1993 Boehling et al.
5,235,261 A * 8/1993 Philipp ..... 318/504
5,244,755 A * 9/1993 Benoist et al. ..... 429/97
5,248,928 A 9/1993 Gilmore
5,263,972 A * 11/1993 Evans et al. ..... 606/176
5,265,343 A * 11/1993 Pascaloff ..... 30/339
5,268,630 A 12/1993 Bhagwat et al.
5,306,285 A * 4/1994 Miller et al. ..... 606/177
5,336,953 A 8/1994 Allemann
5,348,815 A 9/1994 Barker
5,352,969 A 10/1994 Gilmore et al.
5,354,215 A 10/1994 Viracola
5,360,073 A * 11/1994 Akazawa ..... 173/15
5,366,477 A 11/1994 LeMarie, III et al.
5,388,749 A * 2/1995 Davignon et al. ..... 227/67
5,401,592 A 3/1995 Gilpin et al.
5,406,187 A 4/1995 Harrison
5,447,807 A 9/1995 Peled et al.
5,449,997 A 9/1995 Gilmore et al.
5,456,994 A 10/1995 Mita
5,460,906 A 10/1995 Leon et al.
D364,463 S * 11/1995 Pitzen et al. ..... D24/146
5,480,734 A 1/1996 Schulz et al.
5,489,484 A 2/1996 Wheeler et al.
5,504,412 A 4/1996 Chan et al.
5,551,883 A 9/1996 Davis
5,553,675 A 9/1996 Pitzen et al.
5,557,190 A 9/1996 Brotto
5,620,808 A 4/1997 Wheeler et al.
5,626,979 A 5/1997 Mitsui et al.
5,629,602 A 5/1997 Makino
D379,795 S 6/1997 Pitzen et al.
5,642,031 A 6/1997 Brotto
5,789,101 A 8/1998 Wheeler et al.
5,792,573 A 8/1998 Pitzen et al.
5,919,585 A 7/1999 Wheeler et al.
RE37,226 E 6/2001 Wheeler et al.

OTHER PUBLICATIONS

Product brochure entitled: "Mini–Driver Air Instrument System" by 3M, 1975. (4 pages) (No month).*

Product brochure entitled: "Acculan" by Aesculap. (4 pages) (No Date).*

Product brochure entitled: "Cordless Sagittal Saw" by Dyonics. 1984. (2 pages) (No month).*

Product brochure entitled: "The Only Cordless Instrument Powerful Enough to be Stryker", by Stryker ( 4pages) (No date).*

Product brochure entitled: "System 2000 Battery Powered Instruments" by Stryker. 1993 (18 pages) (No month).*

Product brochure entitled: "System 2000 Battery Powered Instruments" by Stryker (11 pages) (No date).*

Instruction Manual entitled: "The Hall Orthair System", by Zimmer USA. (12 pages) (No date).*

Product brochure entitled: "Maxion Cordless Powered Instrument System, Assembly, Operation and Maintenance", by 3M HealthCare (6 pages) (No date).*

Hall Versipower Dual Power Orthopedic Instruments. by Zimmer. 1989 (6 pages) (No month).*

Product Insert entitled "Mark III Electric Tool" by Avery Dennison. (1 page) (No date).*

Operating Instructions entitled, "Mark III Electric Tool", by Avery Dennison, (12 pages) (No Date).*

Japanese Abstract, 1484694, Portable Drills, Aug. 27, 1974, 1 page.

Sony Overseas S.A., DM/011 603 of Aug. 29, 1988, International Design Bulletin, Aug. 1988.

Sony Overseas S.A. DM/029 376 of Apr. 20, 1994, International Design Bulletin, Apr. 1994.

Product Brochure entitled "Maxion™ Cordless Powered Instrument System Assembly, Operation and Maintence," by 3M HealthCare, 31 pages, no date.

Product Brochure entitled "The K–100 Mini–Driver System, Cleaning and Lubrication," by 3M Surgical Products Division, 5 pages, no date.

Product Brochure entitled "Cordless 800 Wire Driver," by Dyonics, 1984, 2 pages, no month.

Product Brochure entitled "Cordless 450 Orthapaedic Drill," by Dyonics, 1984, 2 pages, no month.

Product Brochure entitled "Mini–Driver™ Air Instrument System," by 3M, 1975, 4 pages, no month.

Product Brochure entitled "Acculan," by Aesculap®, 4 pages, no date.

Product Brochure entitled "Cordless Sagittal Saw," by Dyonics, 1984, 2 pages, no month.

Product Brochure entitled "The Only Cordless Instrument Powerful Enough to be Stryker," by Stryker®, 1993, 4 pages, no month.

Product Brochure entitled "System 2000 Heavy Duty Battery Powered Instruments," by Stryker®, 12 pages, no date.

Instruction manual entitled "The Hall® Orthair™ System," by Zimmer USA, 12 pages, no date.

Product Brochure entitled "Maxion™ Cordless Powered Instrument System, Assembly, Operation and Maintenance," by 3M HealthCare, 6 pages, no date.

Product Brochure entitled "Hall® Versipower™ Dual Power Orthopaedic Instruments," by Zimmer, 1989, 6 pages, no month.

Product insert entitled "Mark III Electric Tool," by Avery Dennison, 1 page, no date.

Operating instructions entitled "Mark III Electric Tool," by Avery Dennison, 12 pages, no date.

Product Brochure entitled "The Air Driver II from 3M," by 3M, 2 pages, no date.

Product Brochure entitled "Powered Instrumentation for Large Bone Surgery," by Stryker®, 16 pages, no date.

Product Brochure entitled "Sagittal Saw Attachment," by 3M, 2 pages, no date.

Product Brochure entltled "Cordless 200 Reamer," by Dyonics, 1984, 2 pages, no month.

Product Brochure entitled "System II OrthoPower 90 Battery Powered Surgical Instruments," by Stryker®, 1986, 16 pages, no month.

Maintenance manual and operating instructions entitled "System 2000 Battery Powered Instruments," by Styker®, 1993, 17 pages, no month.

* cited by examiner

COMBINATION RECHARGEABLE, DETACHABLE BATTERY SYSTEM AND POWER TOOL

Matter enclosed in heavy brackets [ ] appears in the original patent but forms no part of this reissue specification; matter printed in italics indicates the additions made by reissue.

[This application is] *This reissue patent application is a continuation of U.S. reissue patent application Ser. No. 09/954,526, filed Mar. 5, 2001, which is a continuation of U.S. reissue patent application Ser. No. 09/637,339, filed Aug. 11, 2000, now abandoned, which is an application for reissue of U.S. patent application Ser. No. 08/692,886, filed Jul. 24, 1996, now U.S. Pat. No. 5,792,573, issued Aug. 11, 1998, which application* is a divisional of U.S. patent application Ser. No. 08/258,338, filed Jun. 10, 1994, now U.S. Pat. No. 5,553,675, issued Sep. 10, 1996.

*Notice: More than one reissue application has been filed for the reissue of U.S. Pat. No. 5,792,573. The reissue applications are: U.S. Reissue application Ser. No. 11/129,760 filed May 16, 2005 (the present application), which is a continuation of U.S. Reissue application Ser. No. 09/954,526 filed Mar. 5, 2001 (pending), which is a continuation of U.S. Reissue application Ser. No. 09/637,339 filed Aug. 11, 2000 (now abandoned).*

TECHNICAL FIELD

The present invention is directed to cordless rechargeable battery powered drive assemblies for driving orthopedic surgical instruments.

BACKGROUND

Orthopedic drive assemblies are well known in the art. Such drive assemblies may be adapted for various orthopedic procedures such as drilling, screwing, reaming, wire driving, pinning and sawing (both reciprocating and sagittal). Typically a drive assembly is powered by either a rechargeable battery system (e.g. a cordless system) or by a pneumatic system which utilizes compressed fluid to power the device.

The art is replete with cordless rechargeable battery powered drive assemblies for driving orthopedic surgical instruments. Typically, such instruments comprise generally pistol-shaped devices having elongate handle and drive portions. Examples of such drive assemblies comprise: (1) the Orthopower 90 cordless instruments available from Stryker of Kalamazoo, Mich.; (2) the Cordless 200 Reamer, Cordless 800 Wire Driver, Cordless Sagittal Saw or Cordless 450 Orthopedic Drill available from Dyonics of Andover Md., (3) the Maxion™ orthopedic drive device, previously sold by the Minnesota Mining and Manufacturing Co. (3M) of St. Paul, Minnesota; (4) the Hall Versipower orthopedic instruments available from Hall Surgical of Carpinerina California (associated with Zimmer); and (5) the product known as the 200 Reamer, previously sold by Black & Decker. Cordless battery powered drive assemblies for driving orthopedic surgical instruments are described in U.S. Pat. Nos. 3,734,207; 4,050,528; 4,091,880; 4,441,563; 4,641,076; 4,728,876 and 5,080,983.

Because the batteries in an orthopedic drive device are preferably rechargeable, releasable attachment means are provided in some prior art devices for releasably attaching a battery pack to the rest of the device. Typically, a battery pack is attached to and removed from the handle portion of the device in a direction that is substantially parallel to the axis of elongation of the handle portion. Individual batteries are placed in a housing creating the battery pack which is then attached to the device by being slid in a direction generally parallel to the elongate axis of the handle portion of the device. The battery pack typically includes electrical circuit connection means for connecting the battery pack to electronic circuitry in the device. A device typically secures the battery pack to the rest of the device.

While such releasable attachment means are generally acceptable, they leave room for improvement. One drawback of such a releasable attachment means is that gravity tends to continuously operate on the battery pack to urge it out of the device. Another drawback for some prior devices is that, because of the significant vibration forces encountered during use of the orthopedic drive assembly (particularly during sagittal sawing), the electrical circuit connection means tend to corrode. This type of corrosion is known as fretting corrosion. As used herein, the phrase "fretting corrosion" means surface degradation occurring at the interface of mating electrical contacts which results in the reduction or even loss of electrical continuity.

Fretting corrosion is found in components forming contacts which are allowed to move independently with respect to each other during current flow. This independent movement is believed to cause mechanical abrasion which will wear the surfaces. Gaping between the electrical contacts during electrical flow may result in electrical arcing with attendant generated heat potentially sufficient to melt the surface of the contacts. Pitting, welding and burning may also result. Also, a physical change in the material forming the contacts may occur. Plating for enhanced electrical contact may be lost and carbon deposits may accumulate resulting in reduced electrical continuity.

Because orthopedic drive assemblies are used in surgical procedures which require delicate yet physically demanding tasks, the balance and maneuverability of an orthopedic drive device is also important to surgeons. Hand fatigue is a problem associated with many existing drive assemblies as well as a general difficulty in maneuvering the device during some surgical procedures. Weight distribution and size considerations are believed to contribute to these problems, as the typical cordless rechargeable battery powered drive assembly may be cumbersome to hold and use, particularly during a delicate orthopedic procedure where only the height quality is tolerated. Size and weight considerations involved in the placement of elements such as the batteries, transmission, electronic control circuitry and motor typically render an existing device to maneuver.

Other prior art drive assemblies are excessively large. Oversized drive assemblies may be difficult to maneuver, particularly during a surgical procedure at a cramped or remote location.

BRIEF DESCRIPTION OF THE INVENTION

According to the present invention there is provided a drive assembly for driving orthopedic surgical instruments which (1) affords excellent balance and maneuverability for a user which offers enhanced handling characteristics and convenience during use, (2) affords attachment and removal of a battery pack in a direction other than the direction of elongation of the handle portion of the device, (3) includes a connection between the battery pack and the electronic circuitry of the device which resists fretting corrosion, (4) includes an ergonomically designed handgrip shape that fits a surgeon's hand comfortably, and (5) is sized for convenient maneuvering during an orthopedic surgical procedure.

According to the present invention, there is provided a drive assembly for driving various orthopedic surgical instruments, such as, but not limited to, drills, screws, reamers, wires, pins and saws (both reciprocating and sagittal). The drive assembly comprises a housing having elongate drive and handle portions with the handle portion projecting from the drive portion. A drive is present comprising an motor preferably mounted within the drive portion. The motor has a motor shaft, and the drive includes a transmission for transmitting power of the motor shaft to the surgical instrument. The transmission includes a drive member. Preferably the drive portion has surfaces defining a wire receiving chamber adapted to receive an orthopedic wire adapted to be driven during an orthopedic surgical procedure.

The drive assembly also includes a trigger assembly movable relative to the handle portion; and electrical circuit means operatively associated with the trigger assembly for controlling the motor.

The handle portion comprises a releasably attachable battery having at least one cell (preferably eight), a battery housing, and a pair of battery contacts. The handle portion also has a battery receiving portion having battery terminals adapted to engage the battery contacts; and releasable attachment means for releasably attaching the battery to the battery receiving portion in a direction other than the direction of elongation of the handle portion. Preferably, the direction is a direction substantially parallel to the axis of the drive portion.

In the preferred embodiment, the releasable attachment means comprises a) the handle portion having a pair of tracks defining flanges that are elongate in a direction substantially parallel to the longitudinal axis of the drive portion, b) the battery having a pair of grooves adapted to receive the flanges of the tracks, and a pair of flexible, resilient cantilever members, and c) the battery receiving portion having surfaces defining a cantilever member cavity for receiving the pair of flexible, resilient cantilever members in an interface fit so that the battery is frictionally held in place relative to the battery receiving portion. A latch for releasably securing the battery to the battery receiving portion is also preferably present.

The drive assembly also includes a novel floating battery terminal assembly comprising biasing means for biasing the battery terminals toward a rest position, and mounting means for mounting the battery terminals for deflection from the rest position. In one embodiment, each of the battery terminals comprises a substantially flat plate member having opposite side surfaces, and each of the battery contacts comprise a pair of flexible, resilient arcuate members which are adapted to engage opposite side surfaces of a battery terminal.

Also preferably, the handle portion comprises a handgrip portion having outer surfaces that are sized and shaped to be grasped by a user without touching the battery, and inner surfaces defining a handgrip cavity. The handgrip cavity is free of the transmission, the motor and any cells of the battery when the battery is received in the battery receiving portion. Preferably, the cells of the battery are spaced on an opposite end of the handgrip portion than the motor and transmission.

Alternatively, the present invention may be described as a rechargeable battery adapted to be repeatedly and releasably attached to an orthopedic drive assembly. In this aspect of the invention, the orthopedic drive assembly has elongate drive and handle portions, a battery receiving portion having a pair of tracks defining flanges, a pair of battery terminals, and surfaces defining a cantilever member receiving cavity.

The battery comprises an autoclave battery housing having opposite top and bottom portions, at least one cell within the battery housing and a pair of battery contacts mounted adjacent the top portion of the housing and adapted to engage the battery terminals of the orthopedic drive assembly. Releasable attachment means are present for releasably attaching the battery to the battery receiving portion in a direction other than the direction of elongation of the handle portion. The releaseable attachment means and battery terminals comprise the preferred versions as discussed above.

In this aspect of the invention, the battery contacts each include a first end fixedly attached to the top portion of the battery housing and a second end adapted to abut a support shoulder of the top portion of the battery housing. The battery housing comprises opposite, substantially flat front and rear walls constructed from a material suitable for protecting the cell(s) during an autoclave procedure. The battery comprises eight substantially cylindrical cells having longitudinal axes. The eight cylindrical cells are arranged in: a) a front row of three cells substantially adjacent a front wall of the battery housing, b) a rear row substantially adjacent a rear wall of the battery housing, and c) a middle row of two cells between the front and rear rows.

BRIEF DESCRIPTION OF THE DRAWINGS

The present invention will be further described with reference to the accompanying drawings wherein like reference numerals refer to like parts in the several views, and wherein.

DETAILED DESCRIPTION

Figure 1:
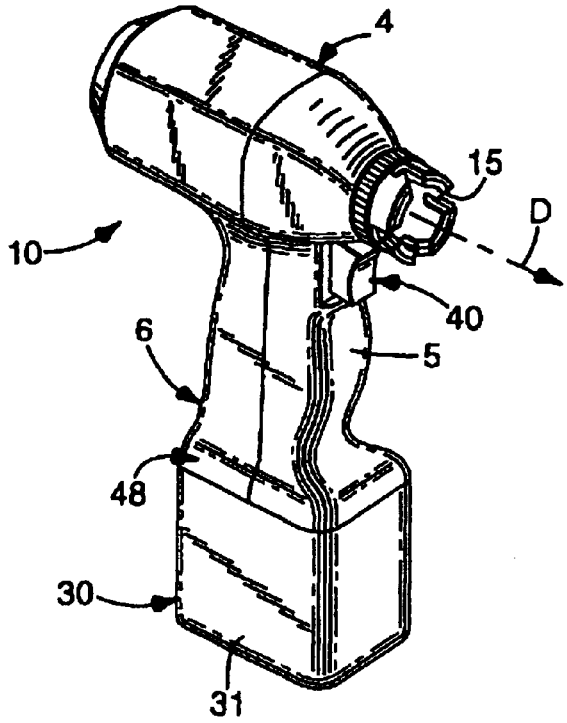
FIG. 1 is a perspective view of a drive assembly for driving orthopedic surgical instruments according to the present invention.
Figure 3:
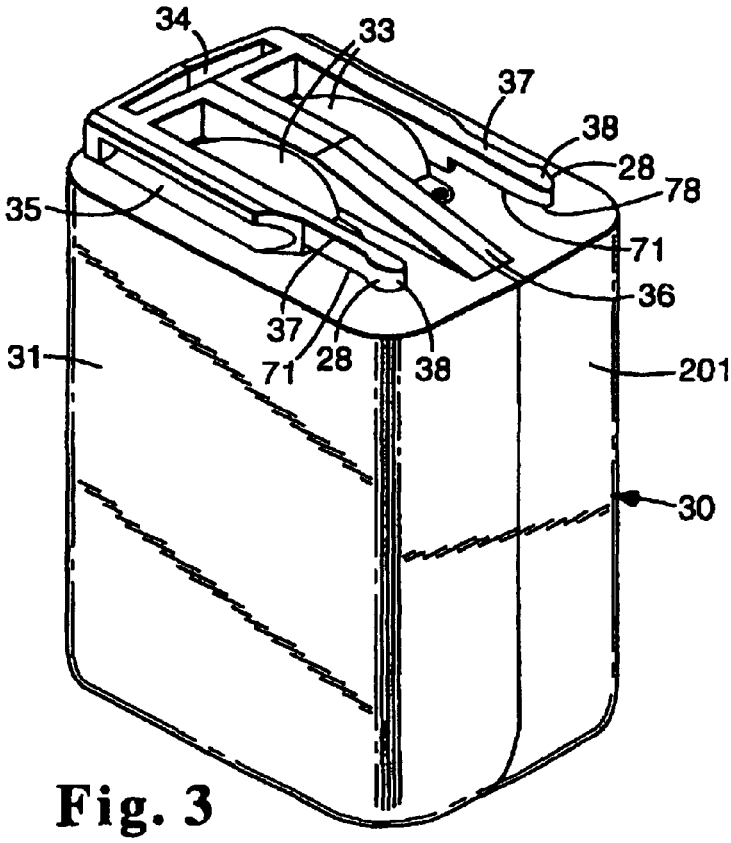
FIG. 3 is an enlarged perspective view of the battery pack for use in the drive assembly of FIG. 1.

Referring now to FIGS. 1 through 10 of the drawing there is shown an embodiment of a cordless rechargeable battery powered drive assembly for driving orthopedic surgical instruments according to the present invention, generally designated by reference character 10. The drive assembly 10 includes a housing comprising elongate drive 4 and handle 6 portions defining drive D and handle H portion longitudinal axes. The drive portion 4 and a significant portion of the handle portion 6 are constructed by assembling two large housing pieces (see FIG. 7) to afford convenient disassembly of the device for repair.

Figure 2:
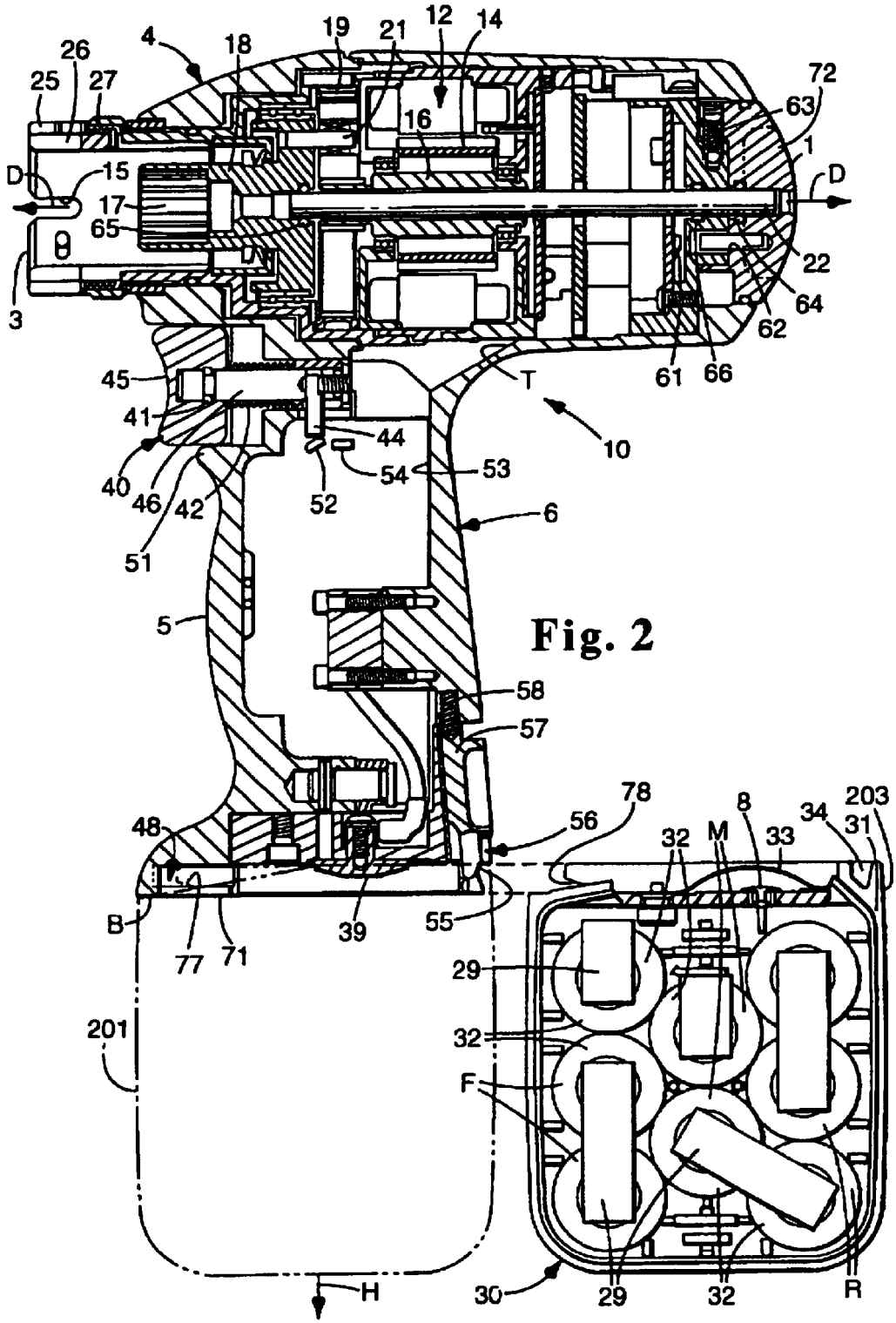
FIG. 2 is an enlarged sectional view of the drive assembly of FIG. 1, illustrating a battery pack of the device removed from the device in solid lines, and illustrating the position of the battery pack when attached to the drive assembly in phantom lines.
Figure 4:
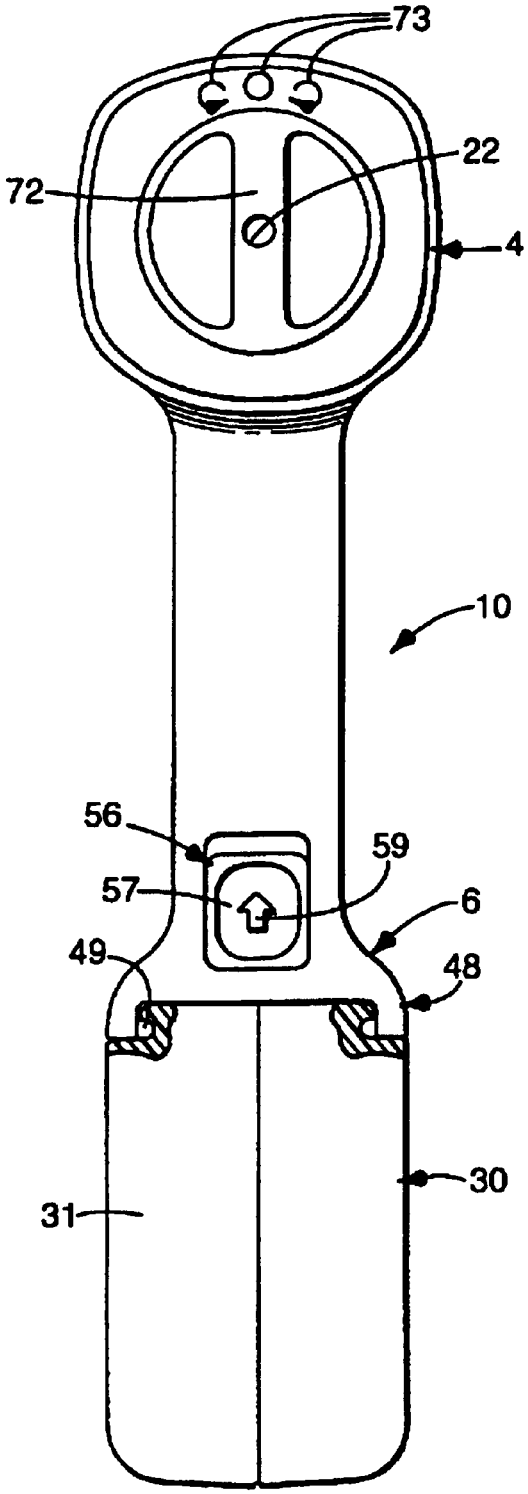
FIG. 4 is an enlarged rear view of the drive assembly of FIG. 1.
Figure 5:
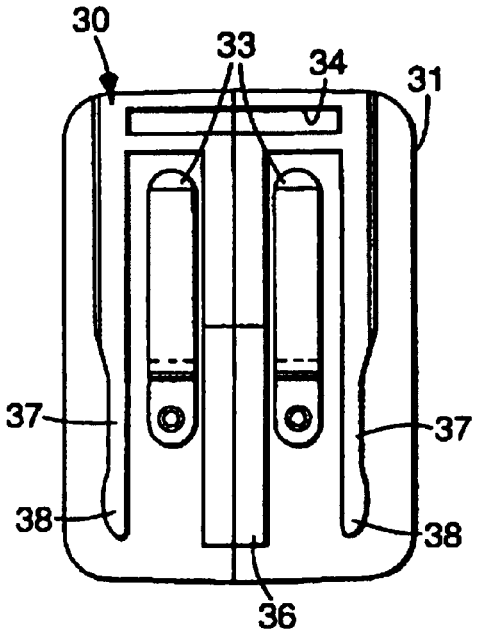
FIG. 5 is a top view of the battery pack of FIG. 3.

Referring now to FIG. 2, the drive assembly 10 includes a motor assembly having a D.C. electric powered motor 12 including a rotor 14 and a motor shaft 16. A drive is also present comprising a transmission for transmitting the power of the motor shaft 16 to the surgical instrument. The illustrated transmission includes a drive member or spindle 18, a ring gear 19, and a gear pin and planetary gear assembly 21.

Preferably, the motor 12 is mounted within the drive portion 4. As used in this application, when it is said that the motor is within the drive portion 4, it is meant that the rotor 14 and motor shaft 16 are substantially completely located within the structure of the housing defining the drive portion 4, as opposed, for example, to one of the rotor or motor shaft being located in the handle portion 6 or a substantial portion of the motor being located in the handle portion 6, of course some wires and electronic circuitry associated with the motor may be present outside the drive portion 4, and yet the motor will nevertheless be within the drive portion 4 as understood in the present invention. Also preferably, the transmission (e.g. 18, 19 and 21) is mounted within the drive portion 4.

A connector is provided for attaching a chuck or other such holder or instrument that may be driven by the drive assembly 10. The connector comprises a nose insert 26 having a socket into which a cylindrical portion of the surgical instrument can project with a splined central rotatable driven collar engaged with mating splines 17 on the inner surface of the drive member 18, and with pins (not shown) projecting radially of the cylindrical portion engaged in longitudinally extending slots 15 opening through the end of the housing. A helix pin/collar assembly 25 is rotatable about the axis D of the drive portion and is biased by torsion spring 27 so that circumferentially projecting hooks near slots 15 on the collar 25 can engage the pins on the surgical instrument to maintain the pins within the slots 15 and thereby the surgical instrument in driven engagement with the drive assembly 10.

The surgical instrument may comprise any instrument suitable for use in an orthopedic surgical procedure, including but not limited to, drills, screws, reamers, pins and saws (both reciprocating and sagittal) or a suitably designed chuck or adapter for use with any of the previously mentioned instruments.

As a particular example, the surgical instrument may comprise the chuck described in U.S. Pat. No. 4,728,876, the entire contents of which are herein expressly incorporated by reference. Alternatively, for example, an appropriate wire driving attachment adapter may be attached to the drive assembly 10 so that it may be used as an orthopedic wire driver, optionally, but not preferably, engagement between the orthopedic wire and the spindle 18 may afford operation of the device 10 as a wire driver.

A stationary member 22 extends from a proximal end 1 of the housing toward its distal end 3. Preferably, the stationary member 22 includes a through chamber so that a surgical wire may be passed through the stationary member 22 from the proximal end 1 of the device 10 toward the distal end 3. The through chamber in the stationary member 22 forms a portion of a wire receiving chamber in the drive portion 4 between the proximal end 1 and the distal end 3. Threading a surgical wire through the wire receiving chamber affords use of the device 10 as a wire driver.

O-rings 64 and 65 restrict internal contamination of the drive assembly 10 from ambient contaminants. O-ring 66 is compressed against member 22 to restrict the member 22 from rotating relative to the handle 6 and drive 4 portions of the housing.

The drive assembly 10 also includes a rechargeable battery or battery pack 30 that is adapted to provide a rechargeable source of power for the motor 12. Unique mounting means (described in greater detail below) attach the battery 30 to the rest of the assembly 10.

A trigger assembly 40 is movable relative to the handle portion 6. The trigger assembly includes a button member 45 adapted to be engaged by a user's digits, a trigger shaft 46, an O-ring seat 41 for fixedly connecting the button member 45 to the trigger shaft 46, a coil spring 42 and magnet 44 that is rigidly attached to the trigger shaft 46. The trigger assembly 40 is movable between a released or extended position (FIG. 2) and a depressed or inner position relative to the handle portion 6.

The drive assembly 10 also includes electrical circuit means operatively associated with the trigger assembly 40 for controlling the motor 12. The illustrated electrical circuit means comprises an on/off hall sensor 52 and a speed control hall sensor 54.

The on/off hall sensor 52 is a digital hall sensor having an output signal with two levels corresponding to an on state and an off state. The on/off hall sensor 52 senses the presence of a magnetic field from the magnet 44 on the trigger assembly 40. When the trigger assembly 40 is released, the magnet 44 is positioned directly over the on/off hall sensor 52 (FIG. 2). The magnetic field of the magnet 44 causes the on/off hall sensor 52 to produce an output signal corresponding to an off state. As the trigger assembly 40 is depressed, the magnet 44 moves away from the on/off hall sensor 52. The on/off hall sensor 52, no longer sensing the presence of a magnetic field, produces an output signal corresponding to an on state.

The output signal from the on/off hall sensor 52 is conditioned by electrical circuitry which provides a standby signal when the on/off hall sensor 52 produces an off signal. The standby signal disables motor drive circuitry and the speed control hall sensor 54. The standby signal therefore ensures that the motor 12 is off whenever the trigger assembly 40 is in a released position (FIG. 2). An added benefit of disabling the motor drive circuitry and the speed control hall sensor 54 is that the electrical power required by the device 10 is significantly reduced during periods when the trigger assembly 40 is not depressed. This current reduction during a standby mode improves energy efficiency of the device 10. In this manner, the device 10 may optionally include a battery saver feature.

The speed control hall sensor 54 is a linear ball sensor which provides a speed control signal having a range of levels based upon the strength of the magnetic field that the variable speed hall sensor 54 detects. As the strength of the magnetic field increases, the speed control hall sensor 54 produces a speed control signal with a higher level. As the trigger assembly 40 is depressed, the magnet 44 moves towards the speed control hall sensor 54 and increases the magnetic field across it. The speed control signal from the speed control hall sensor 54 is conditioned and drives the motor control circuit to provide motor speeds proportional to the speed control signal. Therefore, as the trigger assembly 40 is further depressed, the motor control circuitry increases the motor speed of the drive assembly 10. In this manner, the drive assembly 10 may optionally comprise a variable speed device.

The circuit has a 25 amp current limit to protect the batteries, motor and electronics. The electrical circuit means may optionally include directional drive circuitry which is discussed in greater detail below.

Figure 6:
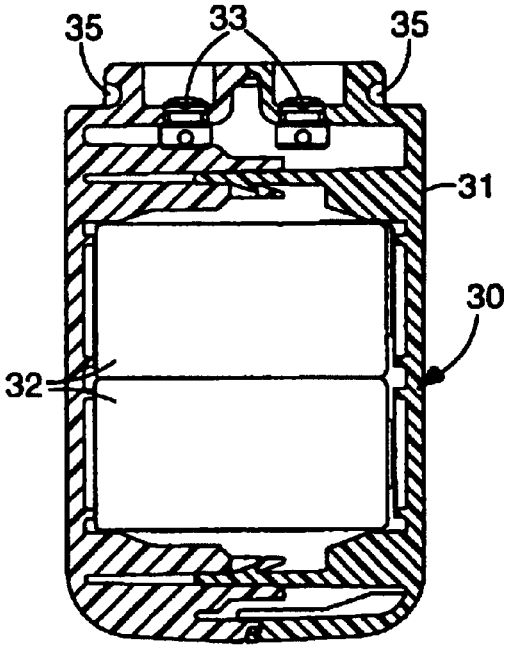
FIG. 6 is a sectional view of the battery pack of FIG. 3.
Figure 6A:
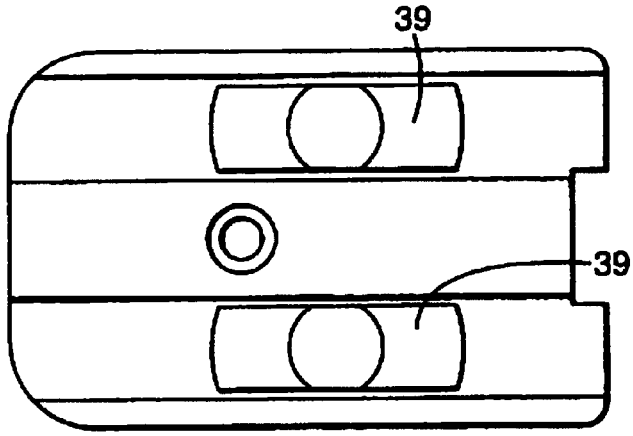
FIG. 6A is a bottom view of portions of the drive assembly of FIG. 2 with the battery pack removed which illustrates battery terminals that are adapted to be connected to the battery contacts of the battery pack of FIG. 3.
Figure 7:
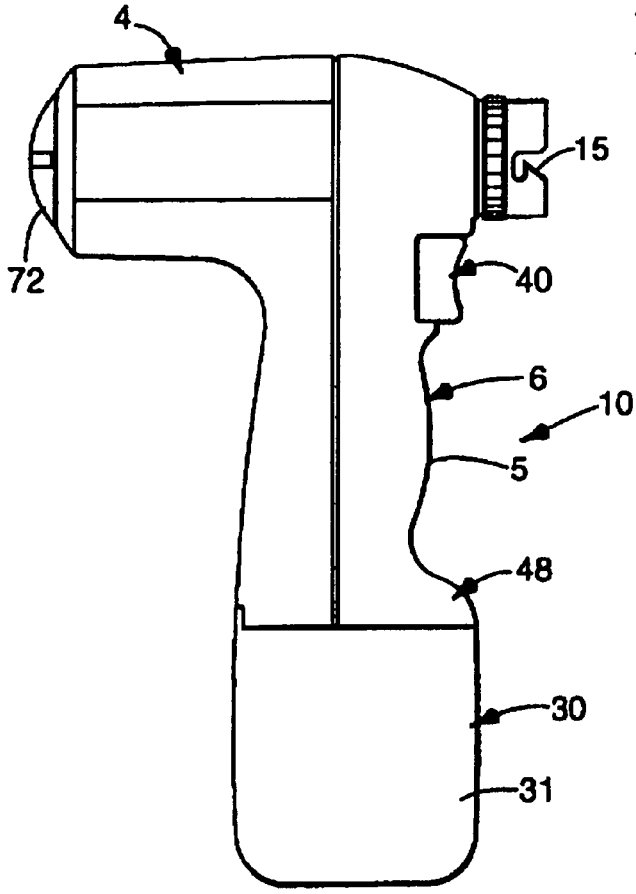
FIG. 7 is an enlarged side view of the drive assembly of FIG. 1.
Figure 8:
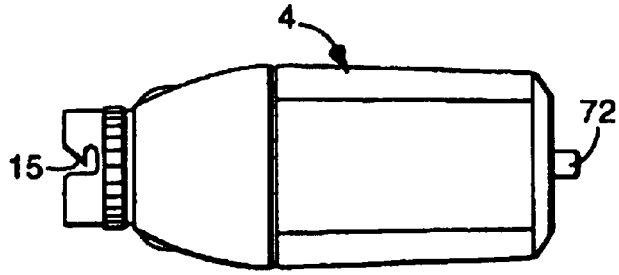
FIG. 8 is a top view of the orthopedic drive assembly of FIG. 7.
Figure 9:
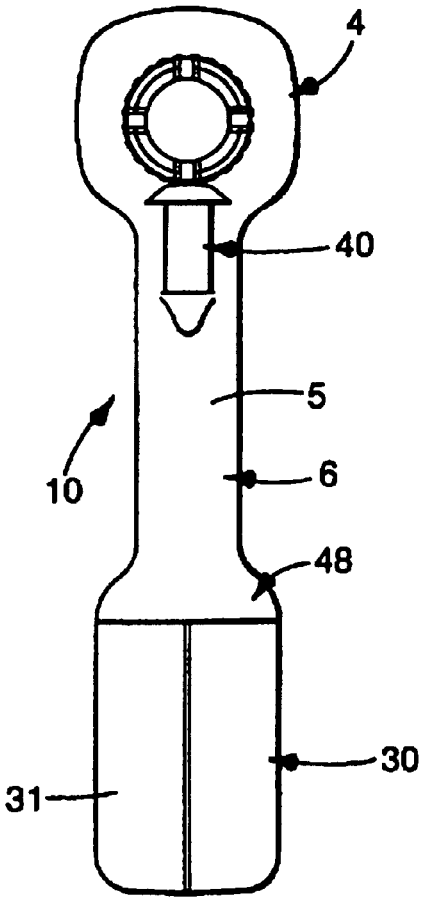
FIG. 9 is a front view of the drive assembly of FIG. 7.
Figure 10:
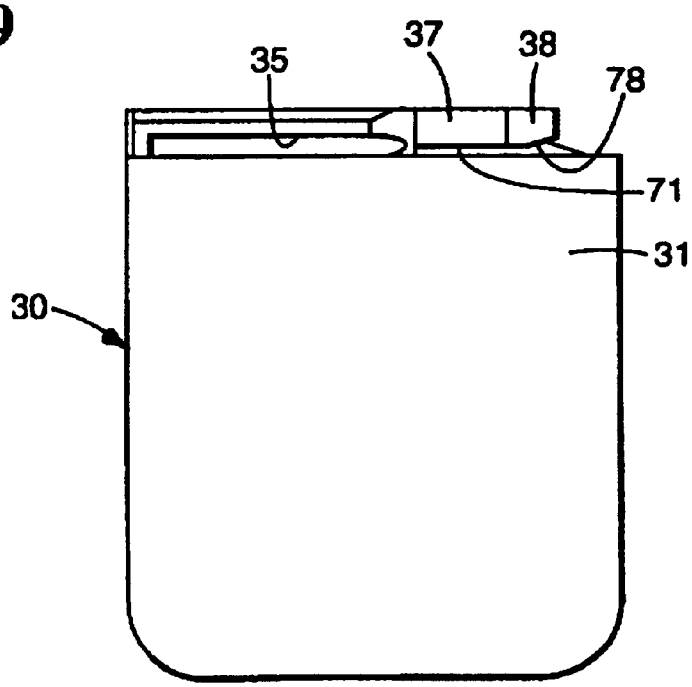
FIG. 10 is a side view of the battery pack of FIG. 3.

As best seen in FIGS. 2 and 6A, the device 10 also comprises battery terminals 39. Each of the battery terminals 39 have three generally flat surfaces including two end surfaces situated at an angle relative to a middle surface. The function of the battery terminals 39 will be described in greater detail below.

The battery terminals 39 may be constructed from any suitable material appropriate for use to construct orthopedic surgical tools. For example, the battery terminals may be constructed from copper, brass, bronze, beryllium copper, stainless steel, steel and aluminum. One or more platings may be present to enhance the electrical conducting and corrosion resisting properties of the battery terminals 39. Examples of such platings include, but are not limited to copper, nickel, gold, silver, tin, electroless nickel, rhodium, sulfamate, nickel, cadmium and zinc.

The handle portion 6 of the device 10 projects (downwardly in FIG. 2) from the drive portion 4 of the device 10. The handle portion 6 of the housing comprises the battery 30 and a handgrip portion 5. The handgrip portion 5 has manually engageable or graspable surfaces and top T and bottom B ends (see FIG. 2). Preferably, the handgrip portion 5 is sized and shaped so that, during use of the device 10, the user does not need to grasp any portion of the battery 30. For example, the handgrip portion 5 may have a height from its bottommost point to the bottom of the drive portion 4 of less than approximately 6 inches (preferably about 4.5 inches), a width of its neck portion of less than about 2.8 inches (preferably about 1.1 inches), and a length of its neck portion of less than about 2.5 inches (preferably about 1.3 inches).

The handgrip portion 5 includes specially shaped surfaces that result in a handle that is comfortably held in the head of a surgeon. A middle part of the handgrip 5 includes an curved front surfaces to form a conveniently held handle. A lip portion 51 is situated adjacent the button member 45 to restrict the chance that a surgeon's glove may be caught between the handle portion 6 and the button 45 when the button 45 is depressed.

As shown in the figures, the width and length of the handgrip portion 5 vary along its height to afford convenient grasping of the device 10. The bottom of the handgrip portion 5 includes a battery receiving portion 48 having the battery terminals 39 adapted to engage battery contacts 33 (described in greater detail below) when the battery 30 is attached to the battery receiving portion 48.

A battery housing 31 (FIGS. 2 and 3) preferably comprises opposite, substantially flat front 201 and rear 203 walls constructed from an autoclavable material. An autoclavable material is a material suitable for protecting battery cell(s) during repeated autoclave procedures. Examples of suitable materials are described below.

The battery 30 comprises at least one rechargeable cell 32 and preferably eight substantially cylindrical cells 32 as shown in FIG. 2. Because the cells 33 are located in a position below or remote from where a user is expected to grasp the drive assembly 10, the handgrip portion is free to be used for mounting other electrical and/or mechanical components such as an electronic printed circuit board forming a portion of the electrical circuit means discussed above.

The battery 30 preferably comprises eight substantially cylindrical cells 32 having longitudinal axes. The axes of the cells are preferably substantially parallel to the front and rear walls 201 and 203. The eight cylindrical cells 32 are arranged in a front row F of three cells substantially adjacent the front wall 201, a rear row R of three cells substantially adjacent the rear wall 203, and a middle row M of two cells between the front and rear rows 201 and 203. All of the rows F, M and R are enclosed within the battery housing 31 so that the cells are protected during an autoclave or other sterilization procedure.

The weight distribution of the device 10 is substantially balanced about the handgrip portion 5 as the relatively heavier elements such as the battery cells and the motor/transmission assemblies of the device 10 are spaced on opposite ends (top T and bottom B) of the handgrip 5. A handgrip cavity 53 is formed within the inner portions the handgrip 5. As opposed to prior art devices which include a battery or motor within the portion of its housing that is designed to be manually grasped, the cavity 53 is free of batteries or motors or transmission or gear assemblies. Since battery cells 30 (described in greater detail below) are situated below the battery receiving portion of the handle portion 6, some of the electronic control circuitry mentioned above may be placed in the handgrip cavity 53 of the handle portion 6. This is believed to further contribute to the beneficial balance and handling characteristics of the device 10.

The cells 32 are preferably stacked in the manner shown in FIG. 2, with a distal row of three cells placed at the front of the battery 30, a proximal row three cells at the rear of the battery 30, and a middle row of two cells placed between the front and rear cells. The axes of the cells are perpendicular to the axis D of the drive portion of the housing. The cells 32 may comprise, for example, nickel-cadmium secondary (rechargeable) sub "C" size cells with a 22 mm diameter and a 34 mm length in a nickel-plated steel case. Such cells are expected to provide a capacity of about 1.4 amp hours at 9.6 volts, D.C. Suitable cells may be obtained from Saft of Valdosta. Ga.; Panasonic of Japan; Sanyo Electric Co. Ltd. of Sumoto-City, Hyogo Japan or Gates available from DC Battery Products of St. Paul, Minn.

The cells 32 are enclosed in an autoclave proof (saturated stream @ 280 degrees Fahrenheit, @ 30 pounds per square inch, and vacuum @ 26 inches of mercury) housing or casing 31. The casing 31 preferably is designed to withstand other sterilization techniques and remain suitable to protect the battery cells 32. The casing 31 includes a poppet or umbrella valve 8 (e.g. the #VL2491-102 Vernay valve generally available from Vernay of Calif.) to relieve any pressure, such as pressure generated by the cells 32. Optionally, the battery housing 31 may include a power terminal (not shown) for a power cord so that the drive assembly 10 may be powered without discharging the cells 32.

The particular material used to construct the casing 31 may comprise any suitable material for use in an orthopedic device. Specific examples include, but are not limited to, poly-ether-imide (PET) including Ultem (e.g. GE grades 1000 Black #7101, 1000 Black #1000, 2100 muddled natural #1000 10% glass fill, 2200 muddled natural 20% glass fill, 3452 muddled natural #1000 45% short glass and mineral, or 6200 muddled natural #1000 20% glass fill high temperature); poly-phenyl-sul-fone (PPSU) (e.g. Amoco Radel R, grades R5100 Black #935 or #937, or R 5000, natural); polysulfone (PSU) (e.g. Amoco Udel P, grade P 1700, natural #11); polyaryletherketone (PAEK) (e.g. BASF Ultrapek, grade KR4176, natural); liquid crystal polymer (LCP) (e.g. Vectra grades A950 natural, A530 muddled natural moderately mineral filled, or A130 muddled natural 30% glass fill); and polyketone (PEK) (e.g. Amoco Kadel E grade 1000 natural).

The motor 12 of the drive assembly 10 is designed to: (1) operate between about 9.6 volts and a reduced voltage which is the output range the battery will produce under load, and (2) have very low internal resistance to restrict internal losses when handling the high current flow by which it is powered. Since the motor 12 and transmission are relatively heavy elements of the device 10 (e.g. the motor may weight about 0.82 pounds), the motor 12 and transmission are preferably located within the drive portion 4 of the housing. Locating the motor 12 and transmission in a position spaced from the handgrip cavity 53 frees the handgrip cavity 53 for use to store the electronic circuitry of the device 10. The location of the motor 12 and transmission also contribute to the beneficial balance and weight distribution of the device 10 and improves its handling characteristics. These improvements are believed to reduce hand fatigue for some users.

The battery 30 shown in FIGS. 1–7, 9 and 10 comprises the battery housing or casing 31, and a pair of battery contacts 33, one of which is an electrically positive terminal, the other of which is an electrically negative terminal. The battery contacts 33 comprise thin, arcuate contact members. The arcuate contact members 33 are connected at one end to the housing 31 and are in electrical communication with the cells 32 (which are connected in series by electrically conductive strips). The other end of the contact members 33 is free to float along the top of the casing 31. Preferably, the contacts 33 are constructed from a flexible, resilient electrically conductive material, such as a material selected from the group comprising copper, brass, bronze, beryllium copper, nickel, stainless steel, aluminum or steel. Optionally, one or more materials may be plated to the contacts to enhance their performance and corrosion resistance. Plating materials include, but are not limited to gold, copper, nickel, silver, tin electroless nickel rhodium, sulfamate nickel, cadmium and/or zinc. The shape of the arcuate contact/members 33 afford their resilient deflection in a direction substantially parallel to the axis H of the handle portion 6 of the housing upon abutment with the battery terminals 39.

Referring now to FIGS. 11, 13–14, 15–16, 18–20 and 24 of the drawings, there is shown a second embodiment of cooperable battery terminals and battery contacts according to the present invention with the battery contacts designated with reference character 33A and the battery terminals designated by reference character 39A.

Figure 16:
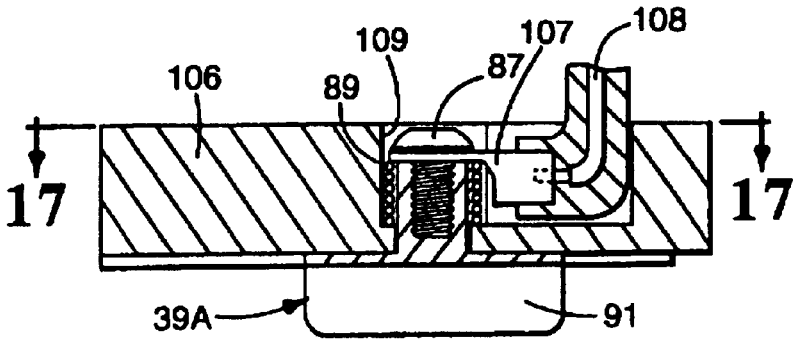
FIG. 16 is a sectional view of a floating battery terminal assembly of FIG. 15 which illustrates details of a battery terminal in a rest position.
Figure 17:
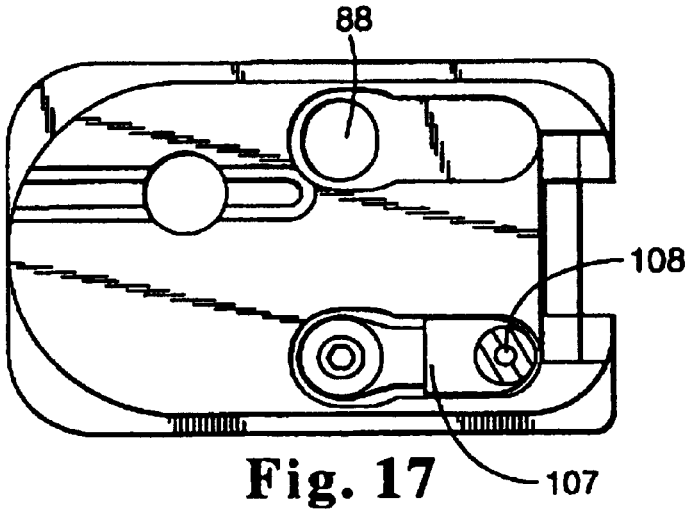
FIG. 17 is a sectional view of portions of the drive assembly of FIG. 16 taken approximately along lines 17—17 of FIG. 16 except that one battery terminal and connector are removed to illustrate details of a hole for receiving the battery terminal.
Figure 18:
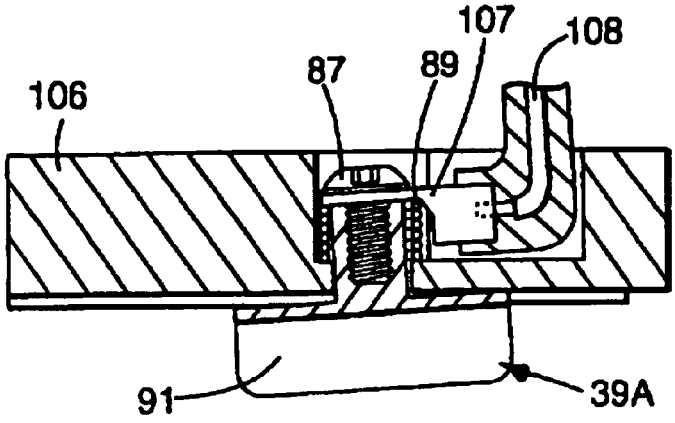
FIG. 18 is a sectional view similar to FIG. 16 except that the floating battery terminal assembly is slightly offset from its rest position, as may occur during vibration of the orthopedic drive device.
Figure 19:
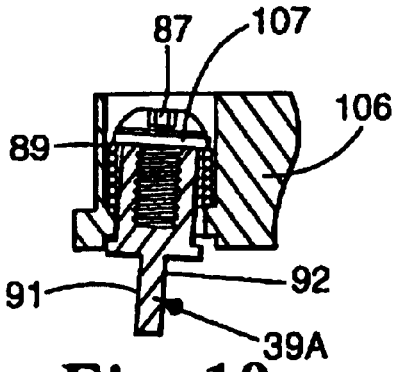
FIG. 19 is a sectional view of the floating battery terminal of FIG. 17 with the battery terminal offset laterally with respect to its longitudinal axis in a rest position and with other portions omitted to illustrate details.

As best seen in FIG. 16, handgrip 5 has a portion constructed from an electrically insulating material 106. The battery terminals 39A are each attached to the insulating material 106 by screw 87. A crimp-on connector 107 is situated between the screw 87 and the battery terminal 39A. The crimp-on connector 107 places the battery terminal 39A in electrical communication with the rest of the electrical circuit means by virtue of insulated wire 108.

The battery terminals 39A are mounted on the manually graspable portion 5 of the housing to float relative to the rest of the housing (including the insulating portion 106). This feature is particularly useful when the device 10 generates vibration as the floating battery terminals 39A tend to retain electrical communication between the battery 30 and the rest of the electronics of the device 10.

The battery terminal 39A is placed in an oblong hole 88 in the handgrip portion 5 of the housing. The oblong hole 88 preferably affords side to side float (movement in a direction that is substantially perpendicular to both axes H and D) of the battery terminal 39A (see FIG. 19), but restricts float of the battery terminal 39A in a direction substantially parallel to the axis D so that the battery terminal 39A is not unduly deflected upon insertion and removal of the battery 30 from the device 10.

Figure 20:
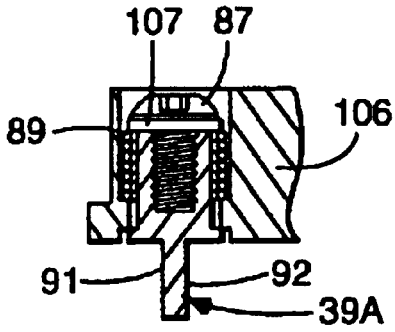
FIG. 20 is a sectional view of the floating battery terminal assembly of FIG. 17 with the battery terminal illustrated in a rest position and with other portions omitted to illustrate details.

A coil spring 89 is provided to afford float of the battery terminal 39A and to bias the battery terminal 39A toward a rest position (see FIGS. 16 and 20). The coil spring 89 has a pair of ends, one of which abuts the crimp-on connector 107, and the other of which abuts the insulating portion 106 of the housing. A rest position of battery terminals 39A is shown in FIG. 16. When the battery terminal 39A is deflected from its rest position (such as when the device 10 vibrates during an orthopedic surgical procedure), the spring 89 deflects in compression from its rest position and biases the battery terminal 39 toward its rest position. Alternatively, the spring 89 may be designed to deflect in tension from its rest position to bias the battery terminal 39 toward its rest position.

The screw 87, crimp-on connector 107, coil spring 89 and portions of the battery terminals 39A are situated within cavity 109 in the handgrip 5. The cavity 109 has a diameter at least slightly larger than the diameter of the screws 87 to afford float of the battery terminals 39A. Unlike the battery terminals 39A, the battery terminals 39A comprise a substantially flat, rectangular contact member having a pair of opposite sides 91 and 92 for contacting the battery contacts 33A.

Figure 13:
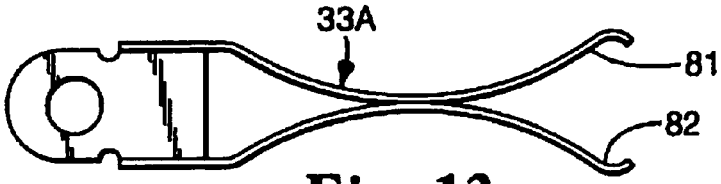
FIG. 13 is a top view of one of a pair of preferred battery contacts for a battery pack according to the present invention, which battery pack is adapted to be connected to a drive assembly having the battery terminals of FIG. 11.
Figure 14:
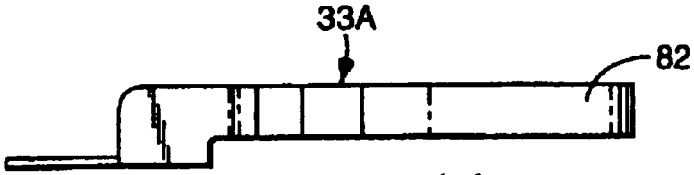
FIG. 14 is a side view of the battery contact of FIG. 13.
Figure 15:
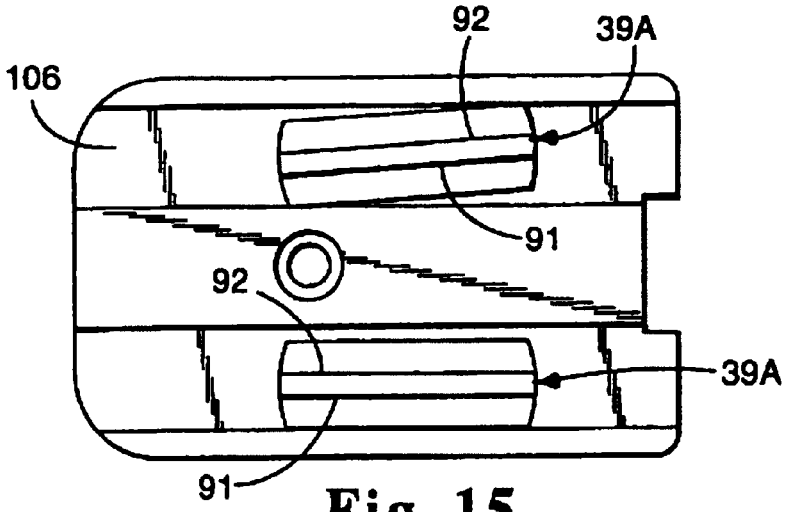
FIG. 15 is an enlarged bottom view of portions of the handle portion of the drive assembly of FIG. 11 which illustrates details of a pair of floating battery terminal assemblies including a battery terminal of one of the assemblies shown offset relative to the axis of the drive portion of the housing of the device.
Figure 24:
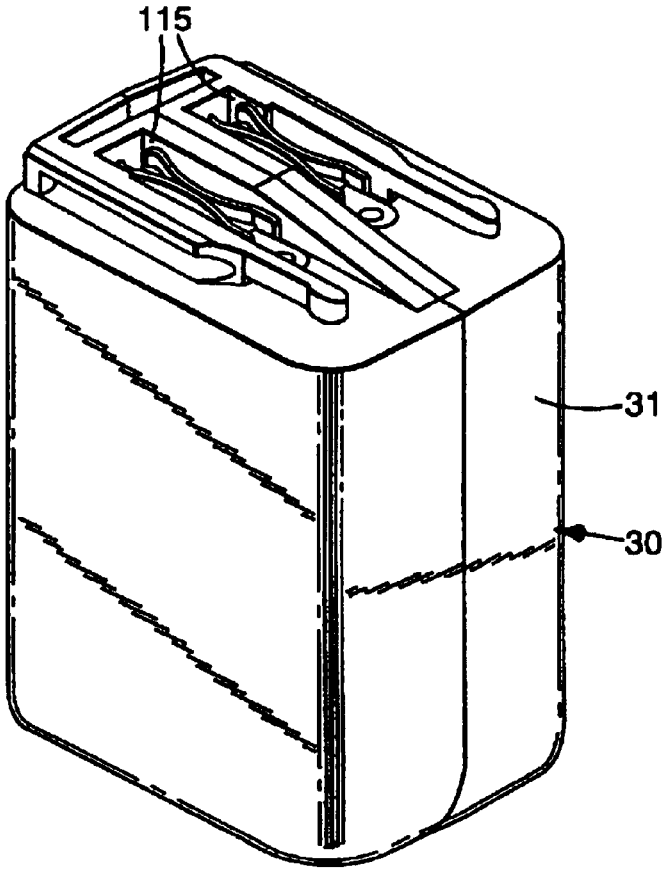
FIG. 24 is a perspective view of a battery with the battery contacts of FIGS. 13 and 14.

Battery contacts 33A for use with the battery terminals 39A is shown in FIGS. 13, 14 and 24. Each of the battery contacts 33A include a pair of flexible, resilient deflecting members 81 and 82. The flexible, resilient deflecting members 81 and 82 each have a first end rigidly affixed to the battery housing 31, and a second end, opposite the first end. The second end of the members 81 and 82 is free to slide along the top of the casing 31 when the members 81 and 82 are deflected. A support shoulder surface 115 of the top portion of the battery housing 31 receives the second end of the members 81 and 82 and affords sliding movement of the second ends of the members 81 and 82.

The battery terminal 39A is designed to be sandwiched between the flexible, resilient deflecting members 81 and 82 and to deflect the members 81 and 82 in a direction that is substantially perpendicular to both of the axes H and D during vibration of the battery terminals 39A. Preferably, side 91 of the battery contact 33A is in electrical communication with deflecting member 81, and side 92 of the battery contact is in electrical communication with deflecting member 82.

The battery contacts 33A are constructed from a flexible, resilient, electrically conductive material. Any of the materials and platings mentioned above for use in constructing the battery contacts 33 may be used to construct the battery contacts 33A. Particular examples include beryllium copper, Brush Wellman alloy 25, 0.0159 (26 Ga) thick, ¼ H temper, or equivalent UNS No. C17200, (ASTM temper TD01) heat treated 2 hours @ 600 degrees fahrenheit (ASTM TH01), R/C 38–43. As an example not intended to be limiting, the contacts 33A may have an overall height in FIG. 14 of about 0.17 inches, a overall length (FIG. 13) of about 1.44 inches and an overall width of approximately 0.32 inches.

Figure 11:
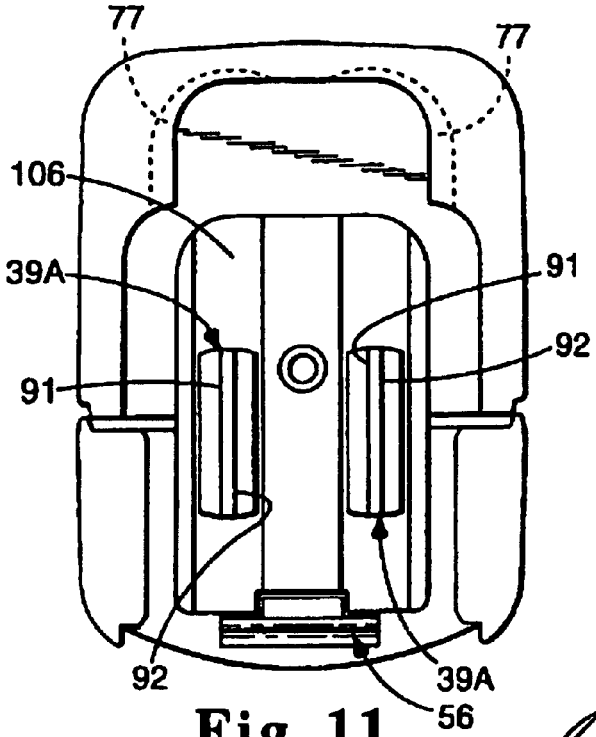
FIG. 11 is an enlarged bottom view of a handle portion of a drive assembly with the battery pack removed to illustrate details of a second embodiment of battery terminals according to the present invention and with portions of a battery pack receiving cavity illustrated with dashed lines.
Figure 22:
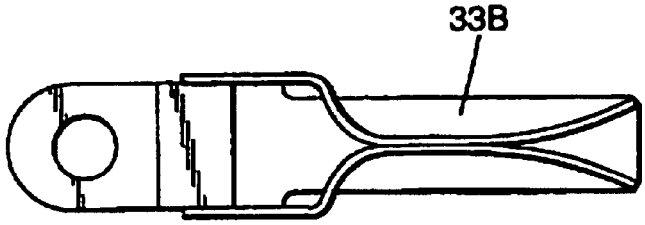
FIG. 22 is a top view of another embodiment of battery contact for use with a drive assembly having the battery terminals of FIG. 11.
Figure 23:
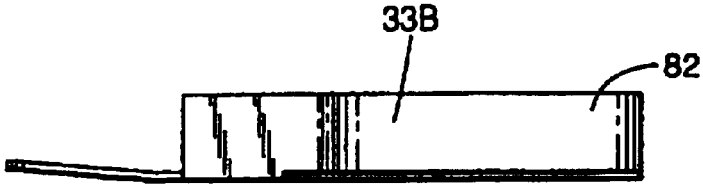
FIG. 23 is a side view of the battery contact of FIG. 22.

FIGS. 22 and 23 illustrate another embodiment of battery contact 33B for use with a drive assembly having the battery terminals of FIG. 11. The battery contact 33B is similar to the battery contact 33A except in that the contact 33B has a slightly different shape when viewed in the top view.

The handle portion 6 of the housing has a releasable attachment means for releasably attaching the battery 30 to the battery receiving portion 48 in a direction other than the direction of elongation of the handle portion 6. In the illustrated embodiment, that means comprises surfaces on the battery receiving portion 48 defining track portions 49 with flanges that are elongate in a direction substantially parallel to the longitudinal axis D of the drive portion. The battery 30 has a pair of opposite mounting grooves 35 adapted to cooperably receive the flanges of the track portions 49 (see FIGS. 4 and 6).

The battery pack 30 also has a pair of flexible, resilient cantilever members 37 having opposite ends. Each of the cantilever members 37 has a first end attached to the battery housing 31 and an enlarged distal end 38. The cantilever members 37 project from the structure defining the grooves 35 in a direction other than direction of elongation of the handle portion 6 (preferably in a direction substantially parallel with the top of the battery and the drive portion axis D). Referring now to FIG. 11, the battery receiving portion 48 of the housing includes a cantilever member receiving cavity 77 formed in part by a relatively thin shelf. The cantilever member receiving cavity 77 includes radiused side walls 75 (see FIG. 12).

Figure 12:
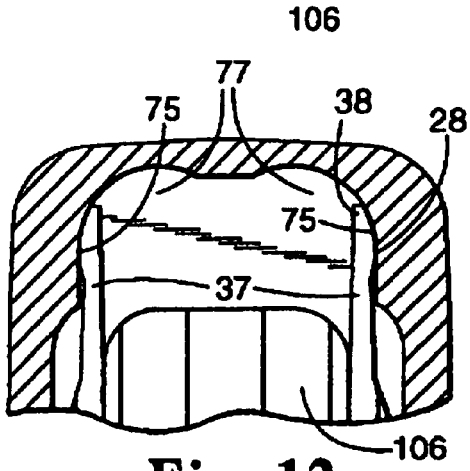
FIG. 12 is a partial sectional view of a battery receiving portion of the drive assembly and cantilever arms of the battery pack showing the position of the cantilever arms when the battery pack is attached to the rest of the orthopedic drive assembly.

The flexible, resilient cantilever members 37 are shown mounted in the cantilever member receiving cavity 77 in FIG. 12. When the battery 30 is mounted on the battery receiving portion 48, the flexible, resilient cantilever members 37 interfere with the surfaces defining the cantilever member receiving cavity 77 to resist movement of the battery 30 relative to the rest of the device 10, particularly movement in the D axis direction. The flanges of the track 49 cooperably engage the grooves 35 and prevent the battery 30 from separating from the rest of the device 10.

The distal ends 38 of the flexible, resilient cantilever members 37 have a bevel 78 to allow them to ramp onto the shelf forming the cavity 77. The engagement between the bevel 78 and the shelf forming the cavity 77 forces the flexible, resilient cantilever members 37 upwards in the H axis direction (in FIG. 2) when the battery 30 is mounted in the battery receiving portion 48. Consequently, the battery 30 is forced into abutment with the manually grasping portion 5. When the battery 30 is fully mounted in the battery receiving portion 48: (1) portion 71 (see FIG. 3) of the battery housing 31 is preferably in contact with the bottom side of the shelf forming the cavity 77, and (2) the flexible, resilient cantilever members 37 are in engagement with the side surfaces forming the cavity 77 which results in a pinching interference fit that tends to resist transmission of vibration to the contacts 33 or 33A. The pinching interference holds the flanges of the track portions 49 in engagement with the grooves 35 of the battery housing 31 to retain the battery 30 attached to the handgrip 5.

The enlarged distal ends 38 of the flexible, resilient cantilever members 37 have an outward biased radius 28. When the battery 30 is inserted into the receiving portion 48 of the handle portion 6, the outward biased radius 28 contacts the radiused side wall 75 (FIG. 12). The width between the outermost portions of the two distal end outward biased radiuses 28 is greater than the width of the radiused side walls 75. With this difference in widths, the flexible, resilient cantilever members 37 are forced inward when the battery 30 is received in the battery receiving portion 48 thereby generating a resistance to movement. For example, the interference is preferably less than about 0.1 inches and is more preferably less than about 0.02 inches. This slight interference causes the resilient members 37 to deflect and to provide excellent frictional contact with the cavity 77 in the battery receiving portion 48. In the manner described above, the cantilever members 37 stabilize the front end of the battery 30. This is especially effective in resisting movement when using the instrument is used for oscillating sawing where side to side forces (perpendicular to the axis H) are generated.

Preferably, the flexible, resilient cantilever members 37 comprise a single, unitary, integral monolithic piece with the battery housing 31. Thus, the material for the battery housing 31 should be sufficiently durable for forming a battery housing (e.g. it should be able to withstand autoclaving procedures), and yet resilient flexible to accomplish the repeated interference fit of the flexible, resilient cantilever members 37 and cavity 77. Any suitable materials may be used including the materials discussed above as suitable for use to construct the casing 31. Alternatively, the flexible, resilient cantilever members 37 may be constructed from a material different than the material used to construct the casing 31.

When the drive assembly 10 is held in the position referenced in FIG. 2, the mounting grooves 35 and flanges of the track portions 49 are cooperable to resist the effect of gravity on the device 10 which, in prior art devices, tends to urge the battery away from contact with the rest of the device. A latch 56 is provided for releasably securing the battery 30 to the battery receiving portion 48, and for retaining the electrical contact between contacts 33 of the battery 30 and the battery terminals 39 (or the terminals 39A with the contacts 33A) of the battery receiving portion 48. The latch 56 comprises a blocking member 57 mounted on the lower portion of the housing 6 for movement between a latched (FIG. 4) and a release position. A coil spring 58 biases the blocking member 57 toward the latched position. The latch 56 also includes the battery housing 31 having surfaces defining slot 34 for receiving a chamfered end 55 of the blocking member 57.

In the latched position, (1) the mounting grooves 35 of the battery 30 are received in the track portions 49 (see FIG. 4) in the battery receiving portion 48, and (2) the chamfered end 55 of the blocking member 57 is biased into engagement with the slot 34 of the battery 30 to lock the battery 30 to the battery receiving portion 48 of the housing. Indicia 59 may be present to provide user information such as how to unlatch the battery 30.

The latch 56 also includes means for automatically moving the blocking member 57 from the latched toward the release position as the battery 30 is mounted to the battery receiving portion 48. That means comprises the battery housing 31 having a ramp surface 36 adapted to engage the chamfered end 55 on the blocking member 57.

Referring to FIG. 2, as the battery 30 is slid into the track portions 49 of the battery receiving portion 48, the ramp surface 36 engages the chamfered end 55 of the blocking member 57 and cams the blocking member 57 toward the release position, thereby enabling the flanges of the track portions 49 to be slid into the corresponding, cooperable grooves 35 of the battery housing 31. Once the battery 30 is fully mounted on the battery receiving portion 48, the chamfered end 55 of the blocking member 57 is biased into engagement with the slot 34 of the battery housing 31 as described above. The side of the blocking member 57 opposite chamfered end 55 is not chamfered to resist inadvertent release of the battery 30.

As a portion of the electrical circuit means mentioned above, the drive assembly 10 also includes a convenient rotary switch means, operated by ribbed member 72 on the proximal end 1 of the drive housing 4 opposite drive member 18, for causing the motor 12 to rotate the drive member 18 either in forward or reverse (clockwise or counterclockwise) directions, or to prevent any rotation by the motor 12 even when the trigger 40 is moved to its inner position. Indicia 73 indicate when the device is in the forward, reverse or stop modes.

Figure 21:
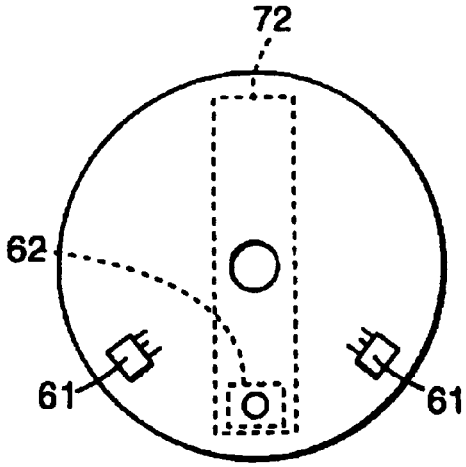
FIG. 21 is a schematic illustration of a switch mechanism for use in the drive assembly according to the present invention.

FIG. 21 is a schematic illustration of the switch means. The motor control switch with forward, off and reverse positions is preferably mounted behind the motor. The motor control switch includes a rotatable knob 72 with an attached magnet 62 and a detent mechanism 63 with three positions that correspond to the forward, off and reverse positions. When the knob is rotated fully clockwise, the magnet 62 by its magnetic field, activates one of two hall sensors 61 to run the motor counter-clockwise when facing the output shaft. When the knob is rotated fully counter-clockwise, it will reverse the motor. A center, neutral (off) position is also included.

The present invention has now been described with reference to several embodiments thereof. It will be apparent to those skilled in the art that many changes or additions can be made in the embodiments described without departing from the scope of the present invention. Thus, the scope of the present invention should not be limited to the structures described in this application, but only by structures described by the language of the claims and the equivalents of those structures.

What is claimed is:

[1. A rechargeable battery adapted to be repeatably and releasably attached to an orthopedic drive assembly, the orthopedic drive assembly having elongate drive and handle portions, a battery receiving portion having a pair of tracks defining flanges, a pair of battery terminals, and a blocking member movable between latched and release positions;

said battery comprising:

an autoclavable battery housing having top and bottom portions, at least one cell within the battery housing and a pair of battery contacts adjacent the top portion of the housing and situated to engage the battery terminals of the orthopedic drive assembly, releasable attachment means for releasably attaching the battery to the battery receiving portion in a direction other than the direction of elongation of the handle portion, said releasable attachment means comprising:

a) the battery having a pair of grooves adapted to receive the flanges of the tracks, and b) a slot for receiving the blocking member when the blocking member is in the latched position.]

[2. A rechargeable battery according to claim 1 wherein each of the battery terminals comprise a substantially flat plate member having opposite side surfaces, and each of said battery contacts comprise a pair of flexible, resilient arcuate members which are adapted to engage opposite side surfaces of a battery terminal.]

[3. A rechargeable battery according to claim 1 wherein said battery contacts each include a first end fixedly attached to said top portion of said battery housing and a second end adapted to abut a support shoulder of the top portion of the battery housing.]

[4. A rechargeable battery according to claim 1 wherein said battery housing comprises opposite, substantially flat front and rear walls constructed from a material suitable for protecting the cell(s) during an autoclave procedure, said battery comprises eight substantially cylindrical cells having longitudinal axes, said eight cylindrical cells being arranged in:

a) a front row of three cells substantially adjacent said front wall within the battery housing, b) a rear row of three cells substantially adjacent said rear wall within the battery housing, and c) a middle row of two cells between said front and rear rows wherein all eight cells are within the battery housing.]

[5. A rechargeable battery according to claim 1 wherein the slot is sized and shaped to engage the blocking member to lock the battery to the battery receiving portion when the blocking member is in the latched position.]

[6. A rechargeable battery according to claim 1 wherein the battery further includes means for automatically moving the blocking member from the latched toward the release position as the battery is mounted to the battery receiving portion.]

[7. A rechargeable battery according to claim 6 wherein the means for automatically moving the blocking member comprises a ramped surface on the top portion of the battery housing.]

[8. A rechargeable battery adapted to be repeatably and releasably attached to an orthopedic drive assembly, the orthopedic drive assembly having elongate drive and handle portions, a battery receiving portion having a pair of tracks defining flanges, a pair of battery terminals, and a blocking member movable between latched and release positions;

said battery comprising a battery housing having top and bottom portions, at least one cell within the battery housing, and a pair of battery contacts adjacent the top portion of the housing and situated to engage the battery terminals of the orthopedic drive assembly when the battery is fully received by the orthopedic drive assembly, releasable attachment means for releasably attaching the battery to the battery receiving portion, said releasable attachment means comprising:

a) the battery having a pair of grooves adapted to receive the flanges of the tracks, and b) a slot for receiving the blocking member when the blocking member is in the latched position, wherein the slot is sized and shaped to engage the blocking member to lock the battery to the battery receiving portion when the blocking member is in the latched position.]

[9. A rechargeable battery according to claim 8 wherein the battery further includes means for automatically moving the blocking member from the latched toward the release position as the battery is mounted to the battery receiving portion.]

[10. A rechargeable battery according to claim 9 wherein the means for automatically moving the blocking member comprises a ramped surface on the top portion of the battery housing.]

[11. A rechargeable battery according to claim 8 wherein each of the battery terminals comprise a substantially flat plate member having opposite side surfaces, and each of said battery contacts comprise a pair of flexible, resilient arcuate members which are adapted to engage opposite side surfaces of a battery terminal.]

[12. A rechargeable battery according to claim 8 wherein said battery contacts each include a first end fixedly attached to said top portion of said battery housing and a second end adapted to abut a support shoulder of the top portion of the battery housing.]

*13. A powered device with a detachable, rechargeable battery comprising:*

*a housing having an electric motor associated therewith, an elongate handgrip portion, and a battery receiving portion attached to a bottom end of the handgrip portion, the battery receiving portion including battery terminals, the battery terminals being electrically connected to the electric motor via a power switch for delivering electric power to the electric motor;*

*a battery comprising a battery casing, at least one rechargeable battery cell housed inside of the battery casing, and battery contacts adapted to contact the battery terminals formed on the housing when the battery is attached to the housing, the at least one rechargeable battery cell being electrically connected to the battery contacts; and*

*wherein one of the housing or the battery casings has a pair of flange formed thereon, and the other of the housing or the battery casing has a pair of mounting grooves formed thereon which engage the pair of flanges in a direction of engagement other than the general direction of elongation of the handgrip portion when the rechargeable battery is mounted to the housing; and*

*wherein the handgrip portion does not house any part of the electric motor.*

*14. The tool of claim 13 wherein a drill chuck is operatively connected to the electric motor to drive a drill.*

*15. The tool of claim 13 further comprising means for releasably securing the battery to the battery receiving portion.*

*16. The tool of claim 13 wherein the rechargeable battery cell comprises at least two electrically connected, individual, rechargeable, cylindrical battery cells arranged in a plurality of rows and housed inside of the battery casing.*

*17. The tool of claim 13 wherein the pair of flanges or the pair of mounting grooves that is formed on the battery casing is at least one-third the length of a top portion of the battery casing.*

*18. The tool of claim 13 wherein the rechargeable battery cell comprises at least five series electrically connected, individual, rechargeable, cylindrical battery cells arranged in a plurality of rows and housed inside of the battery casing; and*

*the pair of flanges or the pair of mounting grooves that is formed on the battery casing is at least one-third the length of a top portion of the battery casing.*

*19. The tool of claim 16 wherein the battery casing comprises two halves joined together, and each of the halves formed approximately a half of a top portion of the battery casing and a half of a bottom portion of the battery casing.*

*20. The tool of claim 16 wherein the pair of flanges is a pair of parallel flanges, and the pair of mounting grooves is a pair of parallel mounting grooves.*

*21. The tool of claim 13 wherein the housing further comprises a motor portion attached to a top end of the handgrip portion opposite the handgrip portion's bottom end, and wherein a longitudinal axis of the handgrip portion intersects the motor portion and the battery receiving portion and the battery casing when the battery is attached to the housing.*

*22. The tool of claim 21 wherein the rechargeable battery cell comprises at least five electrically connected, individual, rechargeable, cylindrical battery cells arranged in a plurality of rows and housed inside of the battery casing.*

*23. The tool of claim 22 wherein the pair of flanges or the pair of mounting grooves that is formed on the battery casing is formed on a top portion of the battery casing opposite a bottom portion with a generally flat bottom surface.*

*24. The tool of claim 22 wherein the battery contacts are positioned on the top portion of the battery casing between the pair of flanges or the pair of mounting grooves that is formed on the battery casing.*

*25. The tool of claim 13 wherein the battery casing further comprises a top portion and an opposite bottom portion, the bottom portion having a substantially flat bottom surface that is parallel to the direction of engagement, and wherein the pair of flanges or the pair of mounting grooves that is formed on the battery casing is formed on the top portion of the battery casing.*

*26. The tool of claim 25 wherein the battery contacts are positioned between the pair of flanges or the pair of mounting grooves that is formed on the battery casing.*

*27. The tool of claim 26 wherein the battery contacts and the battery terminals comprise a substantially flat plate*

*member having opposite side surfaces, and resilient deflecting members which engage the opposite side surfaces of the plate member.*

*28. A powered device with a detachable, rechargeable battery comprising:*

*a housing having an electric motor associated therewith, an elongate handgrip portion, and a battery receiving portion attached to a bottom end of the handgrip portion, the battery receiving portion including battery terminals, the battery terminals being electrically connected to the electric motor via a power switch for delivering electric power to the electric motor;*

*a battery comprising a battery casing, at least one rechargeable battery cell housed inside of the battery casing, and battery contacts adapted to contact the battery terminals formed on the housing when the battery is attached to the housing, the at least one rechargeable battery cell being electrically connected to the battery contacts; and*

*a drill chuck operatively connected to the electric motor to drive a drill;*

*wherein one of the housing or the battery casing has a pair of flanges formed thereon, and the other of the housing or the battery casing has a pair of mounting grooves formed thereon which engage the pair of flanges in a direction of engagement other than the general direction of elongation of the handgrip portion when the rechargeable battery is mounted to the housing.*

*29. The tool of claim 28 wherein the electric motor drives a planetary gear transmission, and the planetary gear transmission drives a drive spindle adapted to mount the drill chuck.*

*30. The tool of claim 28 wherein the rotary axis of the electric motor is parallel to the direction of engagement.*

*31. The tool of claim 28 wherein the rechargeable battery cell comprises at least five electrically connected, individual, rechargeable, cylindrical battery cells arranged in a plurality of rows in a single plane and housed inside of the battery casing.*

*32. The tool of claim 31 wherein the longitudinal axes of all of the battery cells are parallel to each other and perpendicular to the single plane.*

*33. A powered device with a detachable, rechargeable battery comprising:*

*a housing having an electric motor associated therewith, an elongate handgrip portion, and a battery receiving portion attached to a bottom end of the handgrip portion, the battery receiving portion including battery terminals, the battery terminals being electrically connected to the electric motor via a power switch for delivering electric power to the electric motor; and*

*a battery comprising a battery casing, at least five electrically connected, individual, rechargeable, cylindrical battery cells arranged in a plurality of rows in a single plane and housed inside of the battery casing, and battery contacts adapted to contact the battery terminals formed on the housing when the battery is attached to the housing, the battery cells being electrically connected to the battery contacts;*

*wherein one of the housing or the battery casing has a pair of flanges formed thereon, and the other of the housing or the battery casing has a pair of mounting grooves formed thereon which engage the pair of flanges when the rechargeable battery is mounted to the housing.*

*34. The tool of claim 33 wherein a drill chuck is operatively connected to the electric motor to drive a drill.*

*35. The tool of claim 33 further comprising a saw blade mounted for reciprocating motion and driven by the electric motor.*

*36. The tool of claim 33 wherein the pair of flanges is a pair of parallel flanges, and the pair of mounting grooves is a pair of parallel mounting grooves.*

* * * * *